(12) United States Patent
Abramovich et al.

(10) Patent No.: US 9,314,215 B2
(45) Date of Patent: Apr. 19, 2016

(54) DENTAL POSITIONING SYSTEM

(75) Inventors: Mark Abramovich, Brooklyn, NY (US);
Aaron Bratslavsky, Brooklyn, NY (US);
Joe Goldstone, Woodside, NY (US);
Steven Mita, Ossining, NY (US);
Charles Smith, Brooklyn, NY (US)

(73) Assignee: SIRONA DENTAL, INC., Long Island City, NY (US)

( * ) Notice: Subject to any disclaimer, the term of this patent is extended or adjusted under 35 U.S.C. 154(b) by 222 days.

(21) Appl. No.: 13/591,979

(22) Filed: Aug. 22, 2012

(65) Prior Publication Data

US 2014/0056415 A1    Feb. 27, 2014

(51) Int. Cl.
*A61B 6/14*     (2006.01)
*A61B 6/00*     (2006.01)
*G03B 42/04*    (2006.01)

(52) U.S. Cl.
CPC ............ *A61B 6/145* (2013.01); *A61B 6/4435* (2013.01); *G03B 42/042* (2013.01)

(58) Field of Classification Search
CPC ...... G03B 42/042; G03B 42/04; A61B 6/145; A61B 6/4429; A61B 6/4435; A61C 19/04
USPC ................................. 378/168, 169, 170, 208
See application file for complete search history.

(56) References Cited

U.S. PATENT DOCUMENTS

| | | | | |
|---|---|---|---|---|
| 4,554,676 A * | 11/1985 | Maldonado | .......... | G03B 42/042 378/147 |
| 4,965,885 A | 10/1990 | Fuhrmann | | |
| 5,327,477 A * | 7/1994 | Levy | ...................... | A61B 6/145 378/168 |
| 5,652,779 A * | 7/1997 | Levy | ...................... | G03B 42/042 378/168 |
| 6,033,111 A * | 3/2000 | Winters | ............... | G03B 42/042 378/168 |
| 6,190,042 B1 * | 2/2001 | Dove | ...................... | A61B 6/145 378/167 |
| 6,343,875 B1 | 2/2002 | Eppinger et al. | | |
| 6,540,399 B1 | 4/2003 | Eppinger et al. | | |
| 7,425,095 B2 * | 9/2008 | Schmulenson | ...... | G03B 42/042 378/170 |
| 7,427,159 B2 * | 9/2008 | Diederich | ............ | G03B 42/042 378/168 |
| 7,607,831 B2 | 10/2009 | Schmulenson et al. | | |
| 7,661,880 B2 * | 2/2010 | Calderwood | .......... | A61B 6/145 378/167 |
| 7,959,354 B2 | 6/2011 | Steward, Jr. et al. | | |
| 8,016,483 B2 * | 9/2011 | Steward, Jr. | ........... | A61B 6/145 378/168 |
| 8,573,844 B2 * | 11/2013 | Steward, Jr. | ........... | G03B 42/04 378/168 |

(Continued)

FOREIGN PATENT DOCUMENTS

EP    0 119 300 A1    9/1984

OTHER PUBLICATIONS http://www.unigrip.com/pdf/MK358_UG360flyer.pdf "Uni-Grip 360", Jun. 2010, accessed Sep. 13, 2012.

(Continued)

*Primary Examiner* — Wyatt Stoffa
(74) *Attorney, Agent, or Firm* — Fitzpatrick, Cella, Harper & Scinto

(57) ABSTRACT

A dental positioning system and method employing the system are described. The system includes at least one receptor holder having an arm extending from a receptor grip. The receptor grip retains a receptor in a fixed position within the grip and with respect to the arm. The system also includes an alignment ring having a window formed therein and having at least one opening corresponding to the at least one receptor holder. The opening is constructed to receive the arm of the receptor holder such that the receptor is substantially centered with respect to the window.

18 Claims, 17 Drawing Sheets

(56) References Cited

U.S. PATENT DOCUMENTS

| | | | | |
|---|---|---|---|---|
| 2005/0047550 A1* | 3/2005 | Yao | A61B 6/145 | 378/170 |
| 2007/0053497 A1* | 3/2007 | Schmulenson | G03B 42/042 | 378/170 |
| 2008/0095321 A1* | 4/2008 | Calderwood | A61B 6/145 | 378/170 |
| 2010/0166151 A1* | 7/2010 | Schmulenson | G03B 42/042 | 378/167 |
| 2010/0195790 A1 | 8/2010 | Machado et al. | | 378/38 |
| 2011/0051900 A1* | 3/2011 | Steward, Jr. | A61B 6/145 | 378/147 |
| 2011/0164733 A1* | 7/2011 | Steward, Jr. | G03B 42/04 | 378/170 |
| 2013/0071809 A1* | 3/2013 | Kirkpatrick | A61B 6/14 | 433/29 |

OTHER PUBLICATIONS http://www.trolldental.co.uk/Portals/trolldental/product/pdfs/Manual%20TrollByte%20Plus.pdf; "TrollByte Plus Manual"., Apr. 2008, last accessed Sep. 13, 2012.

http://www.duerrdental.de/en/products/imaging/vistaray/, VistaRay Sensor Holder, Feb. 3, 2011; archived at http://web.archive.org/web/20110203042650/http://www.duerrdental.de/en/products/imaging/vistaray/, archive accessed Sep. 13, 2012.

http://www.flowdental.com/catalog/FlowCatalog2005.pdf, "Dental Imaging Catalog", Flow X-Ray, Inc., copyright 2005. last accessed Sep. 13, 2012.

http://www.rinncorp.com/Pdf/Rinn2011Catalog_web.pdf, "Dentsply Rinn 2011 Catalog", copyright 2011, last accessed Sep. 13, 2012.

\* cited by examiner

DENTAL POSITIONING SYSTEM

BACKGROUND

1. Field

The embodiments described herein relate generally to a dental positioning system for electronic and film x-ray examinations, and more particularly to a dental positioning system arranged to center dental films and electronic x-ray sensors with a radiation source.

2. Description of Related Art

Intra-oral radiographs, i.e., "x-ray images", are an important aspect of dental care. Such x-ray images have many uses, including diagnosing cavities and lesions, documenting treatment, and assisting in guiding procedures, among other things. X-ray images may be taken using a receptor to receive x-ray radiation emitted from an x-ray radiation source. Such a receptor may include either x-ray sensitive film or an x-ray sensitive electronic image sensor, such as a digital image sensor.

In the specific case of digital x-ray imaging, a solid state image sensor (such as, for example, an image sensor comprising a charge-coupled device (CCD) or a CMOS active pixel sensor array (APS)) is used as the receptor instead of x-ray film. Such sensors are typically 5-6 mm thick, and often have a cable for communication to a processing unit, such as a computer. Electronic sensors, unlike pieces of film, are re-usable, and are usually covered by a cross-infection barrier, such as a sheath.

Dental intra-oral image receptors are made in several standard sizes. The receptor is positioned in the mouth behind teeth so as to be positioned incident to x-ray radiation emitted from the x-ray radiation source. For example, in many applications it is desirable for the receptor to be positioned substantially perpendicular to the x-ray radiation. If the receptor is not placed and aligned correctly in the patient's mouth, clinically usable x-ray images may not be obtained, which may result in having to take additional x-rays with a corrected receptor alignment. Repeated x-ray images are undesirable because of the additional time, labor, material (in the case of film receptors) and increased exposure of the patient's mouth to radiation.

Although prior art techniques and devices may have the capability to achieve usable x-ray images, there are several problems with existing dental x-ray positioning systems, with respect to both film and electronic receptors, which are not addressed adequately by these techniques. Because accurate positioning of the receptor is difficult, several devices have been proposed to assist dental practitioners, such as dentists and hygienists, in placing and aligning the receptor.

At least one typical dental x-ray positioning system includes three separable pieces: a grip to hold the receptor, which typically has a bite block area, referred to as a bite block; a metal arm, which extends from the grip; and an alignment ring, which attaches to the metal arm from an end of the arm opposite the grip. When positioned in the mouth of a patient, the arm and the alignment ring generally protrude from the mouth and give the practitioner an alignment point on the alignment ring so that the practitioner can position the x-ray radiation source with respect to the positioning system.

An example of such a typical positioning device, which is configured specifically for a digital sensor receptor, is model XCP-DS digital sensor holder, manufactured by Rinncorp. Each XCP-DS digital sensor holder consists of a sensor grip, which includes a bite block upon which a patient can bite down to hold the grip in place in the mouth, a metal arm which has a generally square shaped cross section, and an attachment which has a complimentary square shaped opening to receive the square metal arm. The three pieces of the digital sensor holder are color coded to match together as a group. Each color corresponds to a specific radiographic view, such as bitewing, anterior, posterior, etc. Thus, a practitioner, such as a dental hygienist, seeking to assemble the digital sensor holder for bitewing x-rays will assemble the three color coded pieces together corresponding to bitewing x-rays.

One deficiency of arrangements like the aforementioned model XCP-DS digital sensor holder is that the square shaped opening in the alignment ring that receives the arm permits the practitioner to easily misalign the grip with respect to the attachment since the square opening will receive the arm in any of four, equally spaced, rotational positions. Moreover, because all of the arms of the model XCP-DS digital sensor holder share the same square cross section, a practitioner can physically couple parts of one color, corresponding to one radiographic view, with those of another color, corresponding to a different radiographic view, which may result in the sensor being misaligned with the x-ray source. Moreover, to obtain the various types of x-ray images, multiple three-piece combinations of grip-arm-attachment must be autoclaved, stored, and assembled for use by the practitioner. Often multiple x-rays are taken during a typical dental examination. Thus, the practitioner must be able to carefully assemble the three-piece combination repetitively while ensuring that the parts are properly aligned and not mismatched for the desired radiographic views.

One attempt to address misalignment of the receptor with respect to the x-ray source is described in U.S. Pat. No. 5,327,477 (Levy). Levy describes an x-ray film positioning system shown in FIG. 1A that includes a carrier and a sighting ring that receives the carrier. Annotations are displayed on the sighting ring corresponding to holes in the ring as well as corresponding carriers received in those holes. The film is placed on the carrier as shown in FIG. 3, and is held between a frictional support member and a film support plate. With the film loaded on the carrier, the carrier is inserted into its corresponding annotated hole in the sighting ring so as to position the film within a projection of a window of the ring.

However, one of ordinary skill in the art will appreciate that the arrangements described in Levy do not ensure that the film will be centered with respect to the film support plate, and thus there is no assurance that the film will be centered with the window of the sighting ring. Accordingly, if the film is not centered with the film support plate, even if the carrier is inserted into its corresponding hole in the ring, the film will not be centered with the x-ray source, and, therefore, the x-ray image produced will be off-centered, resulting in the need to take further x-rays, which, as noted above, generally is not desirable.

Thus, conventional positioning devices are prone to causing error in a clinical environment.

SUMMARY

The above and other limitations are overcome by a dental positioning system and method. In accordance with one example embodiment herein, the system includes at least one receptor holder having an arm extending from a receptor grip. The receptor grip retains a receptor in a fixed position within the grip and with respect to the arm. The system also includes an alignment ring having a window formed therein and having at least one opening corresponding to the at least one receptor holder. The opening is constructed to receive the arm of the receptor holder such that the receptor is substantially centered with respect to the window.

In accordance with one example embodiment herein, a dental positioning method is described. The method includes retaining a receptor in a fixed position within a grip and with respect to an arm of a receptor holder, the arm extending from the receptor grip. The method also includes coupling the receptor holder to an alignment ring having a window formed therein and having at least one opening corresponding to the at least one receptor holder. The opening is constructed to receive the arm of the receptor holder such that the receptor is substantially centered with respect to the window.

In one embodiment retaining further includes seating the receptor in the fixed position by inserting the receptor in the grip and engaging the receptor with an interference member extending from the grip. The interference member is constructed to interfere with the receptor when the receptor is seated in the grip.

Additional features and benefits of the exemplary embodiments described herein will become apparent from the detailed description, figures and claims set forth below.

BRIEF DESCRIPTION OF THE DRAWINGS

The teachings claimed and/or described herein are further described in terms of exemplary embodiments. These exemplary embodiments are described in detail with reference to the drawings. These embodiments are non limiting exemplary embodiments, wherein:

DETAILED DESCRIPTION

One example aspect herein is a dental radiographic positioning system comprised of an alignment ring and one or more receptor holders, as shown in the example embodiments of FIGS. 1A-1C, and 3A to 6B. The example embodiment shown in FIGS. 1A-1C will first be described. Of course, those of ordinary skill in the art will appreciate from a consideration of the following description that the system is not limited to the details of the configuration shown in FIGS. 1A-1C, which is merely exemplary.

Figure 1A:
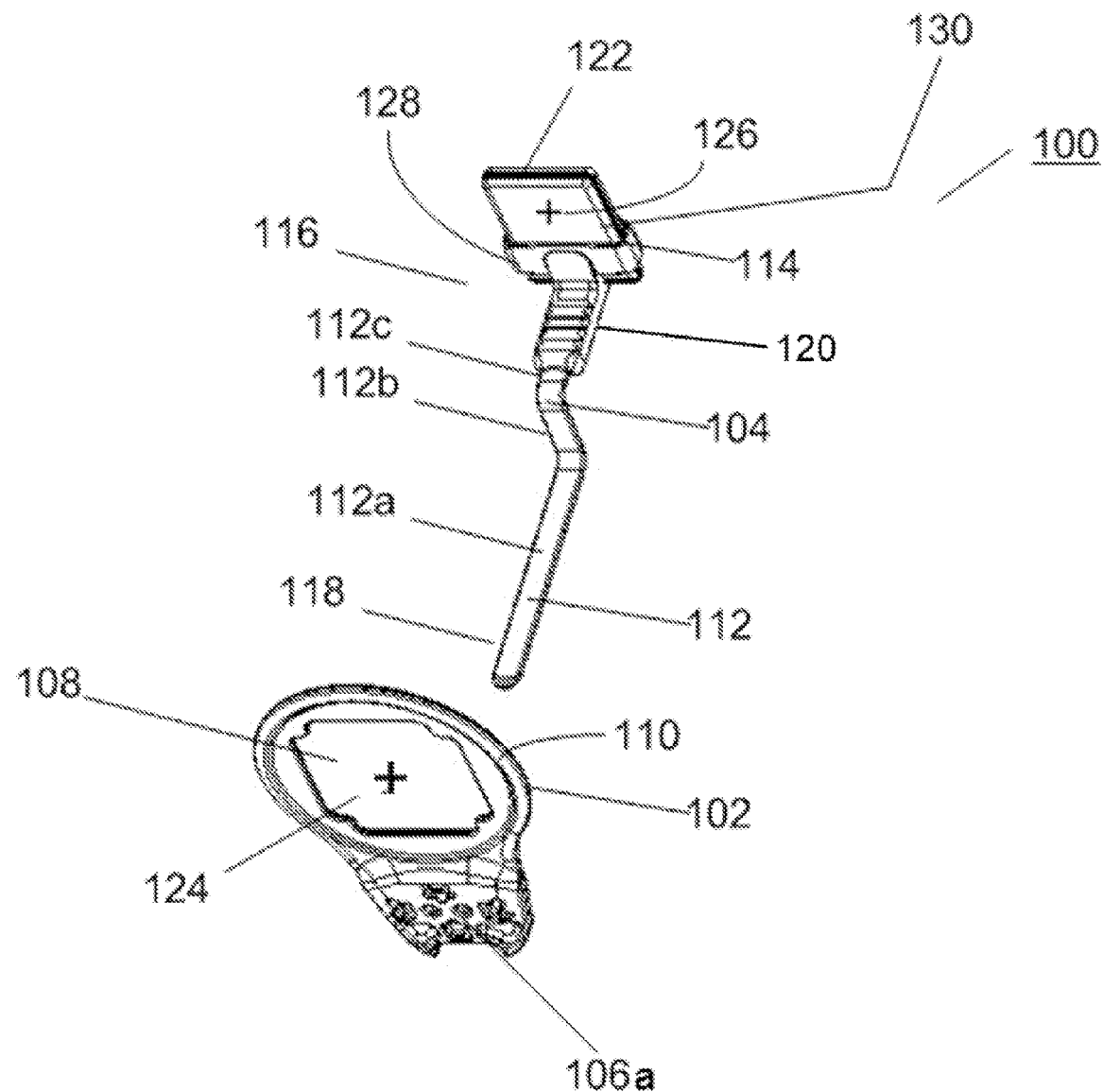
FIG. 1A illustrates an isometric assembly view of an embodiment of a dental positioning system, as viewed from a perspective looking towards a side, rear, and top thereof, in accordance with an example aspect herein.
Figure 1B:
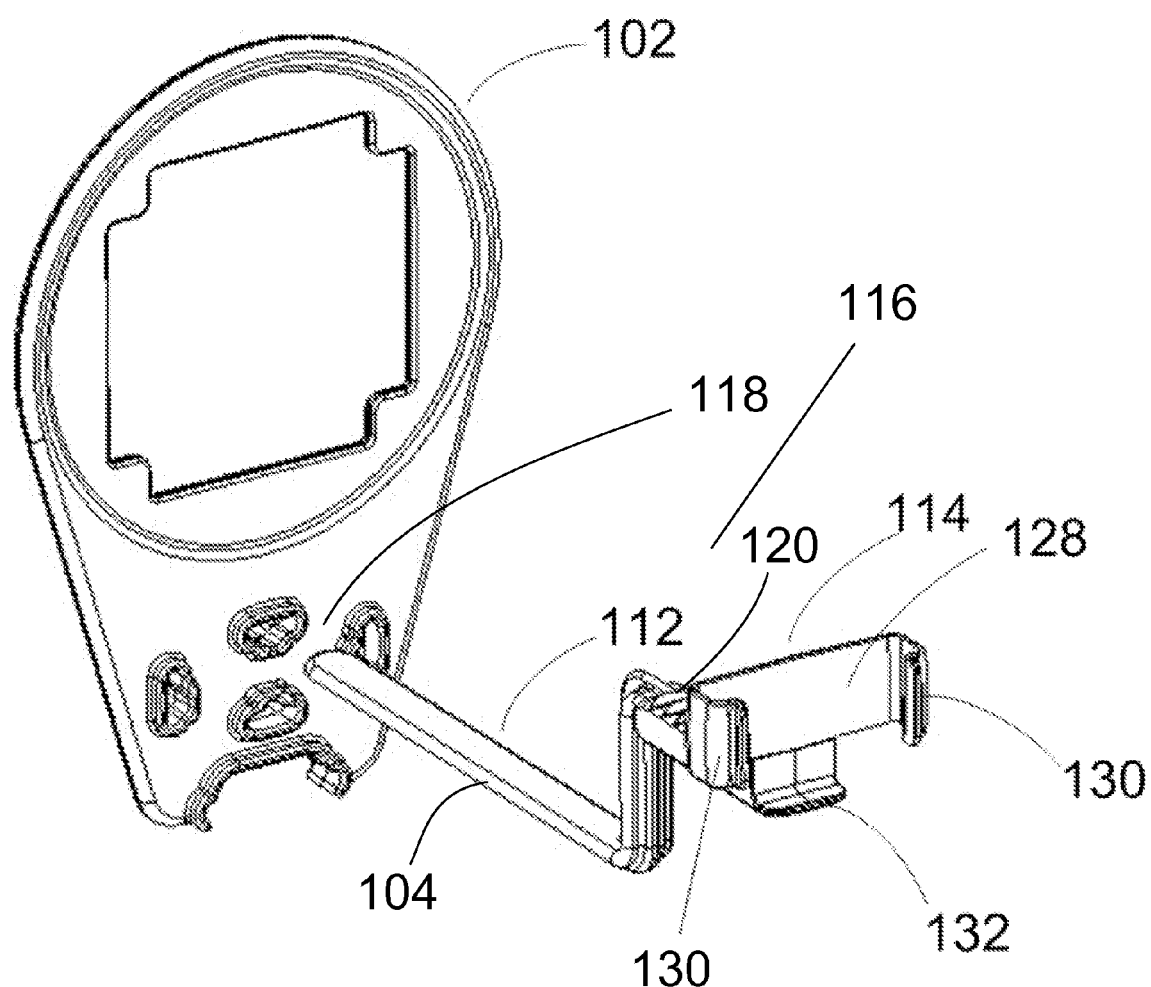
FIG. 1B illustrates the dental positioning system shown in FIG. 1A, as viewed from another perspective.
Figure 1C:
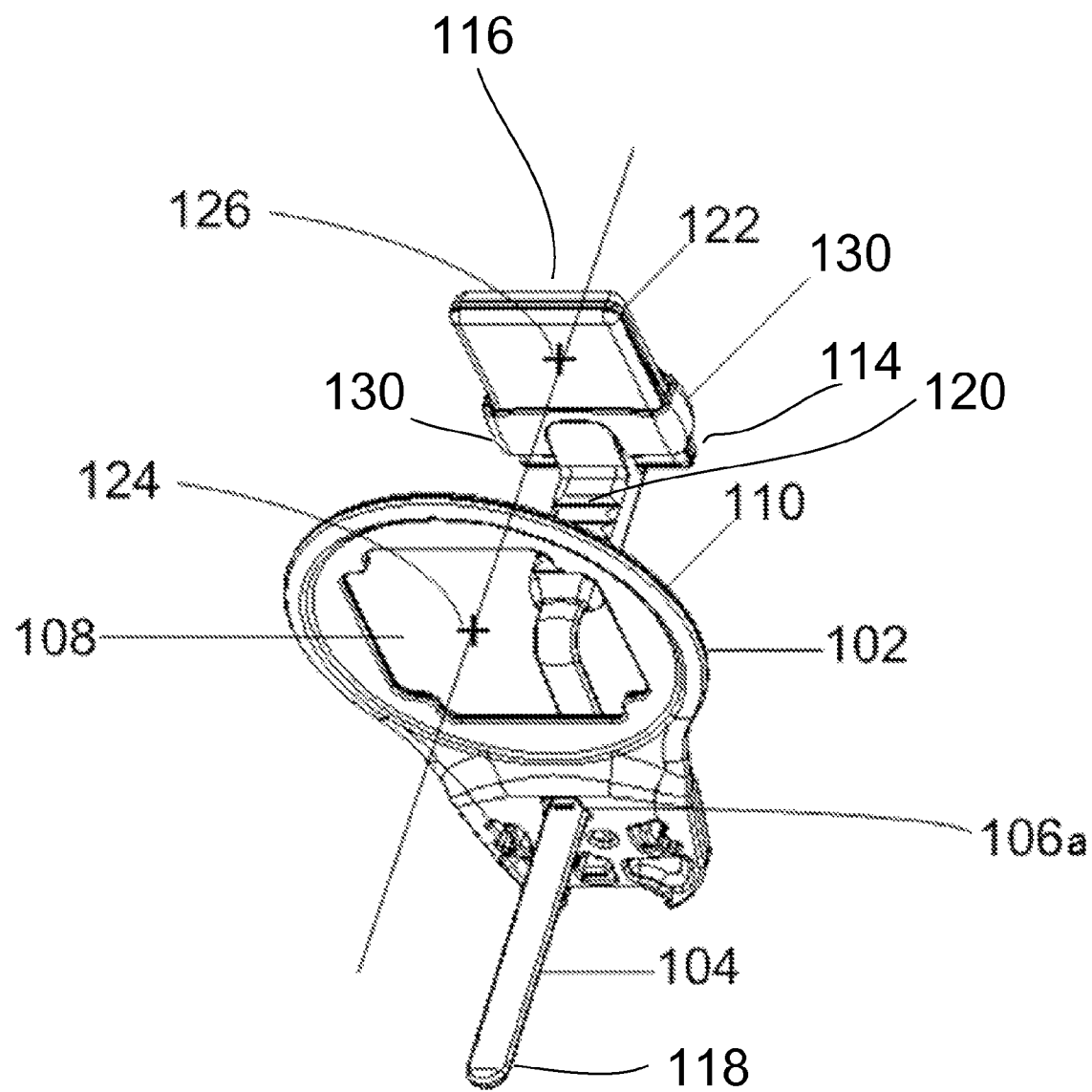
FIG. 1C illustrates a perspective view of the dental positioning system shown in FIG. 1A in an assembled condition, and in which the system is arranged for anterior x-ray images.
Figure 2:
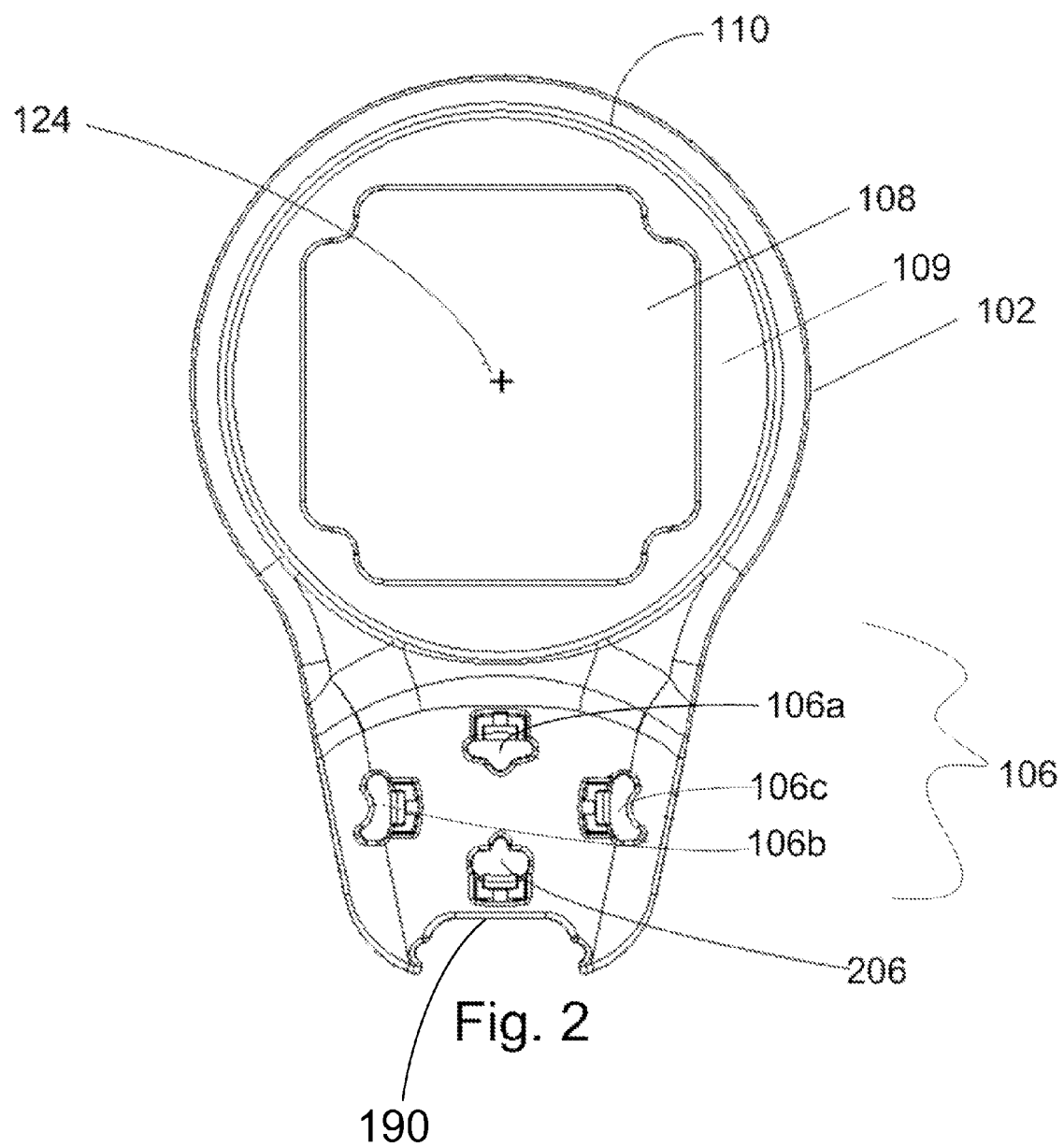
FIG. 2 is an elevation view of an alignment ring illustrated in FIGS. 1A to 1C, viewed from a perspective looking towards a rear side thereof.

FIGS. 1A-1C show an embodiment of the dental radiographic positioning system 100 shown with an alignment ring 102 and a receptor holder 104. In FIG. 1C, the receptor holder 104 is received by the alignment ring 102, while in FIGS. 1A and 1B, the receptor holder 104 is spaced from the alignment ring 102. The alignment ring 102 is shown in greater detail in FIG. 2.

The alignment ring 102 has a generally planar form with a plurality of openings 106, each for receiving a receptor holder 104 therein, such as a holder 104 shown in FIGS. 1A to 1C. The alignment ring 102 also has a window 108 beside the plurality of openings 106. The window 108 has a generally square or rectangular shape which is surrounded by a circular or curved ridged rim 110 which is used to align with a corresponding shaped portion of a radiation source (not shown).

The alignment ring 102 includes a frame 109 interposed between the rim 110 and the window 108. The frame 109 centers window 108 within the rim 110. In one embodiment, the frame 109 is constructed as a radiation shield which can direct radiation from the radiation source substantially through the window 108 of the alignment ring 102 during receptor 122 exposure. Some radiation sources have collimators to also filter and direct the radiation from the radiation source toward a receptor. As discussed herein, a digital sensor can be used as a receptor. Typically, such sensors are manufactured having square or rectangular shapes, such as, for example, the CDR Elite digital sensor, manufactured by Schick Technologies Inc. The shape of the collimator is often matched to the shape of the receptor, so that the collimator will have a square of rectangular shape similar to the shape of the receptor. Thus, in one example embodiment, the polygonal window 108 shown in FIGS. 1A-1C can be aligned with a collimator having a matching polygonal shape on the radiation source (not shown).

The alignment ring 102 also has a notch 190 formed along an outer edge adjacent to an opening 206. The notch 190 is constructed to receive a portion of a communications device (not shown), such as a wireless transmitter, that can communicate with a digital sensor arranged, for example, as the receptor 122 in FIG. 1A. One example of such a communication device which can be received in notch 190 and be connected to ring 102 is a Schick WiFi device manufactured by Schick Technologies Inc.

The receptor holder 104 positions the receptor 122 (FIGS. 1A and 1C) for taking anterior x-ray images when the receptor holder 104 is assembled with the alignment ring 102 as shown in FIG. 1C. The receptor holder 104 has an arm 112 (FIG. 1B) with a grip 114 at an end 116 of the arm. The arm 112 of the receptor holder 104 is constructed to be received in an opening 106a of the alignment ring 102 corresponding to the receptor holder 104 as described below.

In the embodiment shown in FIGS. 1A-1C, the arm 112 of the receptor holder 104 extends from a free end 118 in a direction toward the grip 114. The receptor holder 104, in one example embodiment, is constructed for sliding movement in opening 106a, and may be further constructed along with the opening 106a so as to be retained in opening 106a by a friction fit. For example, the free end 118 of the arm 112 can be aligned with opening 116a and inserted into and through opening 116a. The arm 112 is suitably formed and dimensioned to dispose the grip 114 at a position with respect to the window 108 such that when the receptor 122 is seated in the grip 114 and the arm 112 is inserted into opening 106a, the center 124 of the window 108 will be aligned with the center 126 of the receptor 122. (FIG. 1C).

As shown in FIG. 1A, the arm 112 has a first portion 112a extending from the free end 118, a second portion 112b extending from the first portion 112a, and a third portion 112c extending from the second portion 112b to the grip 114 at end 116. The first and third portions, 112a and 112c, respectively, extend generally perpendicular to the generally planar surface of the alignment ring 102 and the second portion 112b extends generally parallel to the surface of the alignment ring 102 and perpendicular to the first and third portions, 112a and 112c, of the arm 112. The first, second, and third portions lie in a vertical plane that passes through the center of window 108.

The receptor holder 104 can be inserted into the alignment ring 102 through the upper keyed opening 106a as shown in FIG. 1C. The cross section of the first portion 112a of the receptor holder 104 has a profile shape matching that of opening 116a of the alignment ring 102. Thus, in at least one embodiment, there may be a one-to-one correspondence between the receptor holder 104 and opening 106a in the alignment ring 102. Furthermore, by virtue of the matching asymmetrical shapes of the opening 106a and the arm 112, the arm 112 is keyed so that it can be inserted only one way in the opening 106a. This keyed arrangement further reduces positioning errors when the alignment ring 102 and receptor holder 104 are coupled together.

The opening 106a may also be arranged to restrict entry of the arm 112 of holder 104 from only one side of the opening 106a. Such restriction may further reduce the opportunity for a user to incorrectly couple the receptor holder 104 and alignment ring 102 together.

Extending from the third portion 112c of the arm 112, along upper and lower (not shown) surfaces, is a grooved bite block 120 which receives pressure from a patient's teeth to retain the bite block 120. When the receptor holder 104 is inserted into a patient's mouth, the patient bites down on the surfaces of the bite block 120 to retain the receptor holder 104 in position. The sensor grip 114 extends from the third portion 112c of the arm 112, and is arranged to grip a planar receptor 122 such that the receptor 122 extends in a plane parallel with the plane of the alignment ring 102, and substantially perpendicular to a direction of radiation that would be emitted from the radiation source (not shown) aligned at the rim 110 of the alignment ring 102.

The grip 114 described hereinbelow is generally termed an "edge-grip". The grip 114 has a support base 128 from which extends a pair of fingers 130 and a tab 132, shown most clearly in FIG. 1B. The fingers 130 are constructed to be resilient to permit the edges of the receptor 122 to be held firmly in position between the fingers 130, as shown in FIGS. 1A and 1C. That is, the fingers 130 apply pressure to the edges of the receptor 122 to retain the receptor 122 in a fixed position in the grip 114. It will be appreciated that the grip 114 can be sized to accommodate receptors 122 of different sizes, such as sizes 0, 1, and 2, with a sheath (not shown for clarity of illustration) covering the receptor 122. Where the receptor 122 is a digital sensor, the grip 114 can accommodate sensors such as the aforementioned Schick CDR Elite Sensor which have a sensor active area that has sizes corresponding to the active area of one of size 0, 1, and 2 film receptors. The tab 132 contacts the receptor 122 at a third edge thereof when the receptor 122 is fully seated in the grip 114. While the receptor 122 is positioned between the fingers 130 of the grip 114, the receptor 122 can be translated into engagement with the tab 132 so that the receptor 122 is fully seated in the grip 114. Thus, the tab 132 acts as a physical stop or interference member which provides confirmation to a user that the receptor 122 is fully seated in the grip 114. When fully seated in the grip 114, and when the receptor holder 104 is received in its corresponding opening 106a in the alignment ring 102 (FIG. 2), the center 126 of the receptor 122 is aligned with the center 124 of the window 108.

The following describes one way in which a user might use the system 100. In one embodiment, a user desiring to obtain anterior x-ray images can select receptor holder 104 and can insert receptor 122 in the grip 114 between its fingers 130. The user can then translate the receptor 122 in the grip 114 towards the tab 132 so that the receptor 122 engages the tab 132. When the receptor 122 is gripped between the fingers 130 and engages the tab 132 the receptor is determined to be seated in the grip 114. The user can then insert the free end 118 of the arm 112 of the receptor holder 104 into opening 106a in the alignment ring 102 to couple the receptor holder 104 and the alignment ring 102 together. The coupled system 100 can then be at least partly inserted into a patient's mouth by placing end 116 in the mouth first and positioning the bite block 120 between the patient's teeth at the suitable anatomical location to obtain anterior x-ray images. When the patient bites down on the bite block 120 the user may adjust the distance between the grip 114 and the alignment ring 102 as necessary before aligning the radiation source (not shown) with rim 110 and window 108. With the system 100 so disposed, the center 126 of the receptor 122 is aligned with the center of the window 124.

Figure 3A:
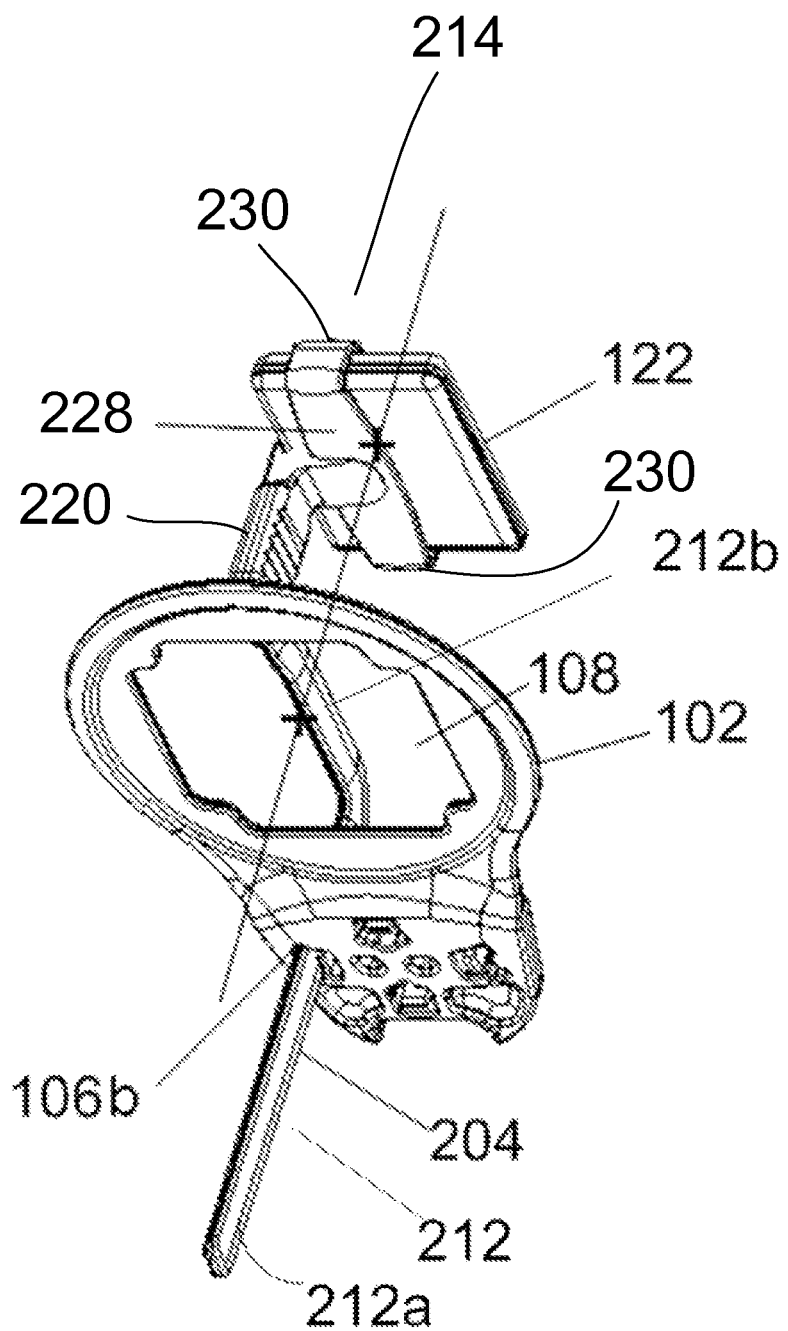
FIG. 3A illustrates an isometric view of another embodiment of a dental positioning system, shown in an assembled condition, as viewed from a perspective looking towards a side, rear, and top thereof, in accordance with an example aspect herein, and in which the system is arranged for right-posterior x-ray images.

FIGS. 3A-3D show an embodiment of the positioning system 100 where the receptor holder 104 of FIGS. 1A-1C is substituted with another receptor holder 204, which is constructed to obtain a right-posterior x-ray view. The receptor holder 204 has an arm 212 which curves generally in a horizontal plane, whereas the arm 112 of holder 104 curves generally in a vertical plane that is transverse to the horizontal plane. Moreover, the arm 212 has a cross sectional profile which extends generally in the vertical direction, whereas arm 112 has a profile that extends in the horizontal direction. The receptor holder 204 includes a grip 214 that is substantially the same as grip 114, except that grip 214 is adapted to seat the receptor 122 in a different orientation to obtain right-posterior x-ray images. As shown in FIG. 3A, for example, grip 214 orients the receptor 122 so that it is placed in an orientation that is offset ninety degrees as compared to the orientation shown in FIG. 1A.

Figure 3B:
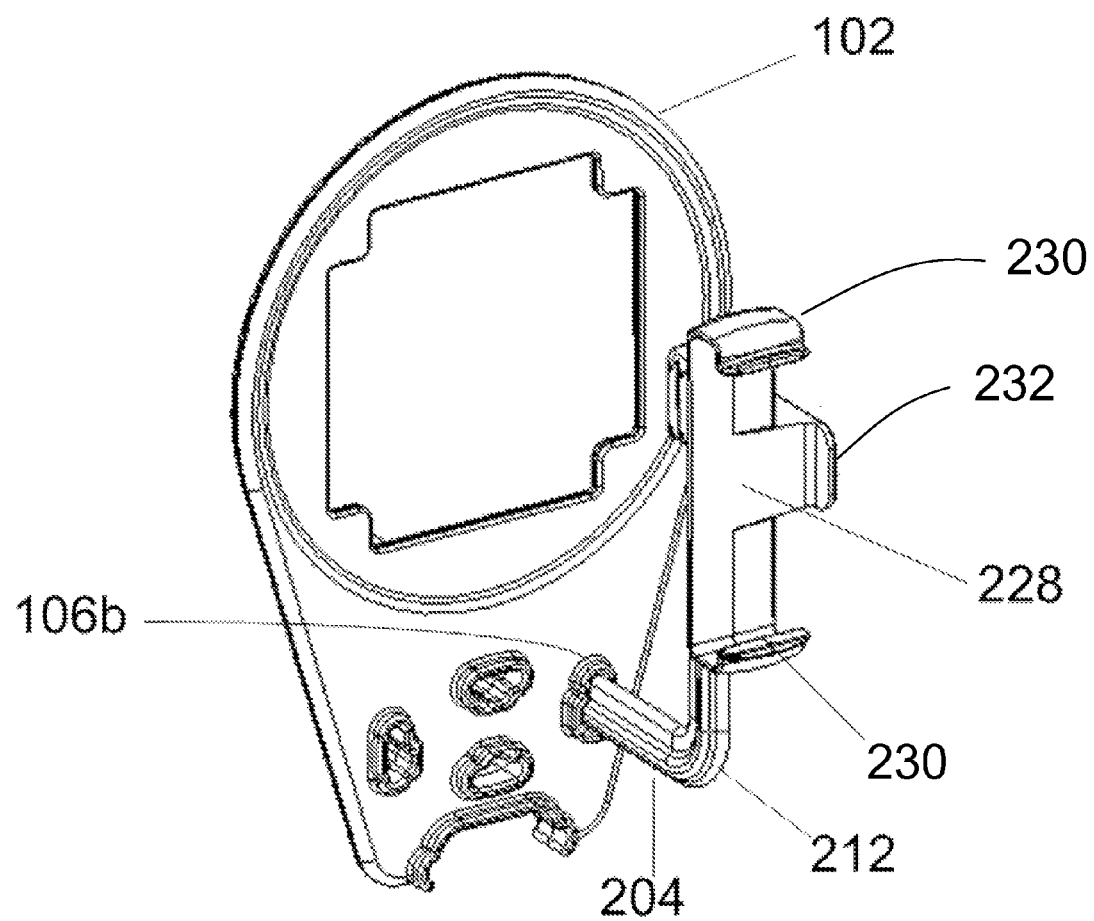
FIG. 3B illustrates the dental positioning system shown in FIG. 3A, as viewed from another perspective.
Figure 3C:
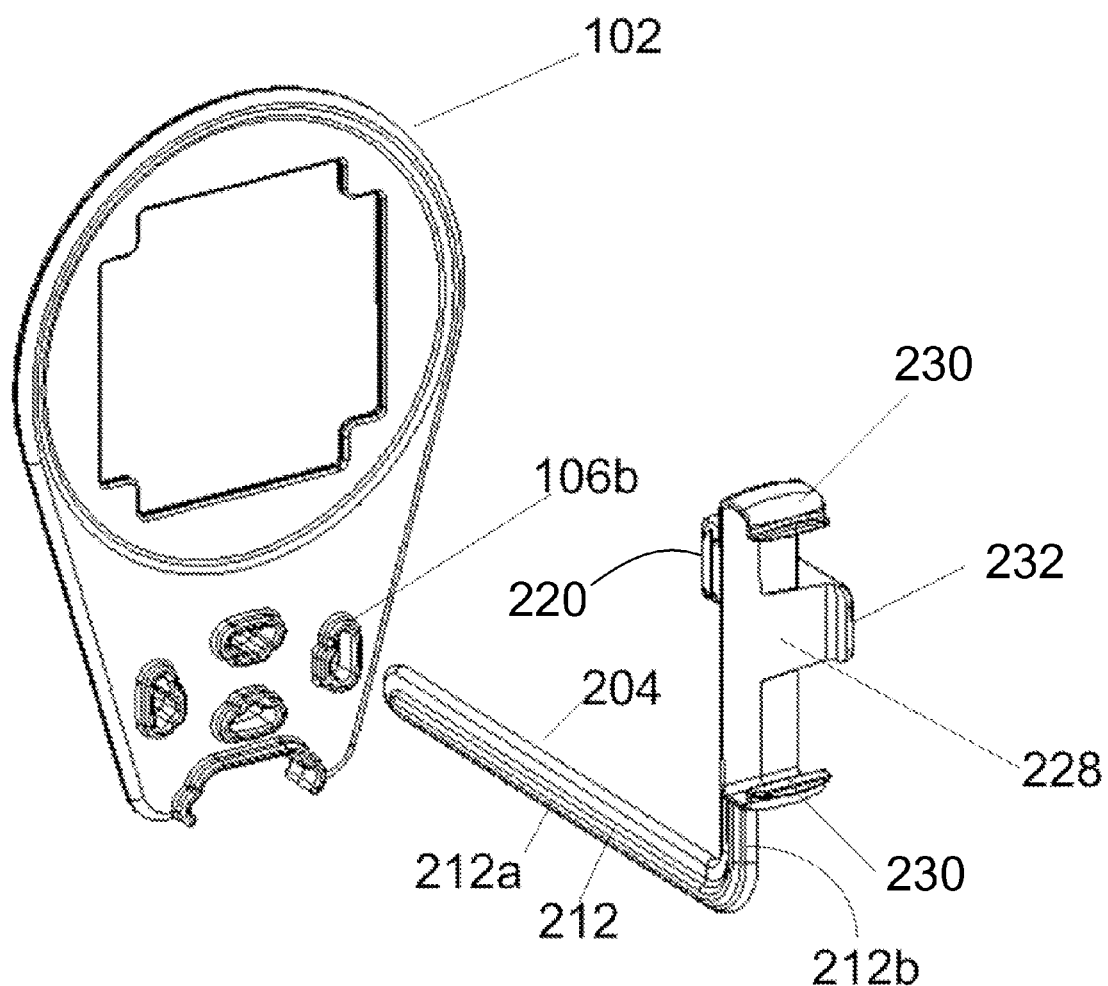
FIG. 3C illustrates an isometric assembly view of the dental positioning system shown in FIG. 3B.
Figure 3D:
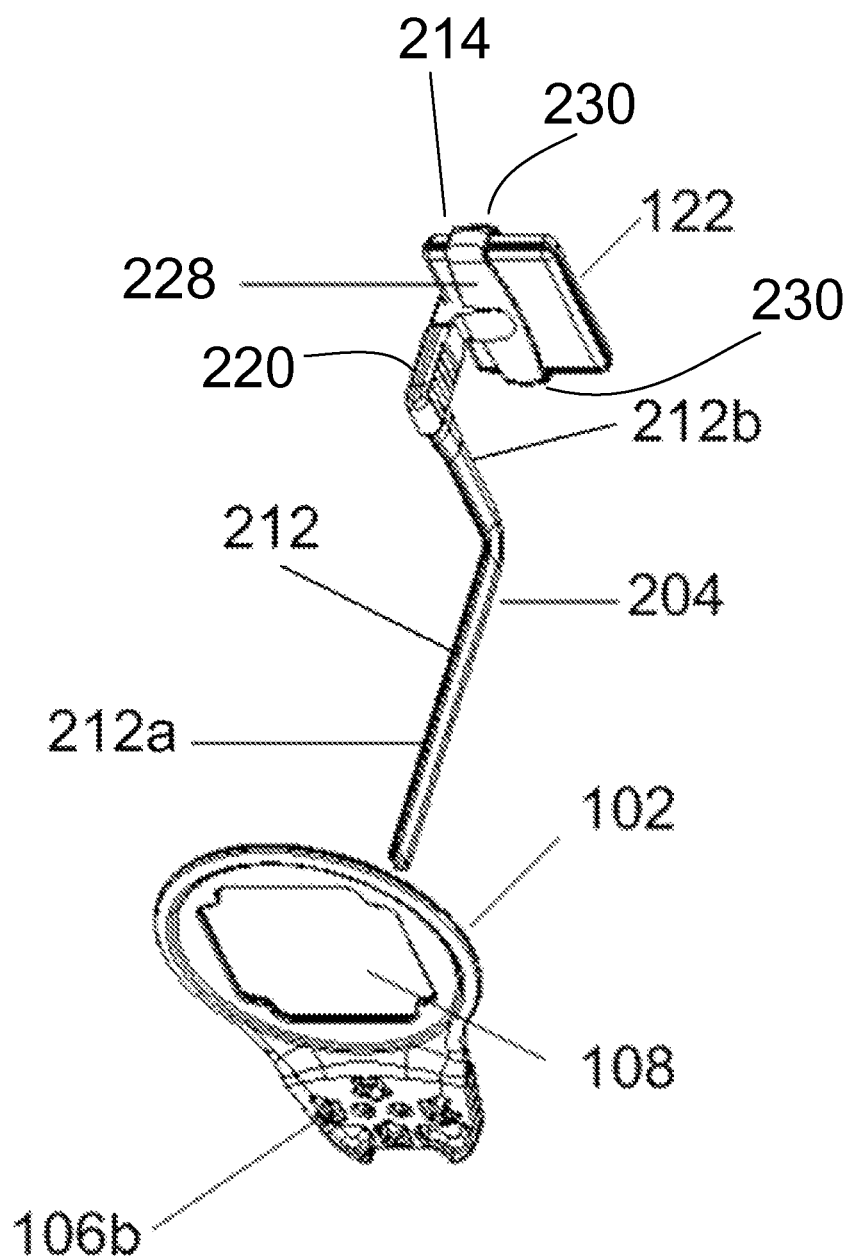
FIG. 3D illustrates another isometric assembly view of the dental positioning system shown in FIG. 3A.

For example, in the embodiment shown in FIGS. 3A-3D, the grip 214 includes a base 228 from which resilient fingers 230 extend to apply pressure to the rectangular receptor 122 along its two shorter edges (FIGS. 3A and 3D). Nevertheless, the grip 214 includes a tab 232 (FIGS. 3B and 3C) which contacts the receptor 122 along its longer edge. The grip 214 is otherwise constructed similarly to grip 114 to seat the receptor 122 in a fixed position so that when the receptor holder 204 is received in opening 106b of the alignment ring 102 the receptor 122 will be centered with the window 108.

FIGS. 3C and 3D show the arm 212 of holder 204 aligned with opening 106b and spaced from the alignment ring 102. As shown in FIGS. 3A and 3B, the receptor holder 204 is received in opening 106b of the alignment ring 102. The arm 212 has a first portion 212a and a second portion 212b, which in one embodiment extend at a right angle with respect to each other. In one embodiment, the first portion 212a has a cross section that matches the shape of the opening 106b in alignment ring 102. In this manner the arm 212 of receptor holder 204 may be keyed with the opening 106b, in similar manner to the arrangement of arm 112 and opening 106a described herein with respect to the embodiment shown in FIGS. 1A-1C.

Adjacent the grip 214 there is bite block 220 that has ridged surfaces like those of bite block 120 except that the ridged surfaces of bite block 220 are oriented perpendicular to those surface of bite block 120.

FIGS. 4A-4D show an embodiment of the positioning system 100 where the receptor holder 204 of FIGS. 3A-3D is substituted with another receptor holder 304 which is constructed to obtain a left-posterior x-ray view, which is the opposite view obtained by holder 214. The holder 304 includes grip 214, which extends to the left in FIGS. 4A and 4C, as compared to the right in FIGS. 3A-3D.

Figure 4A:
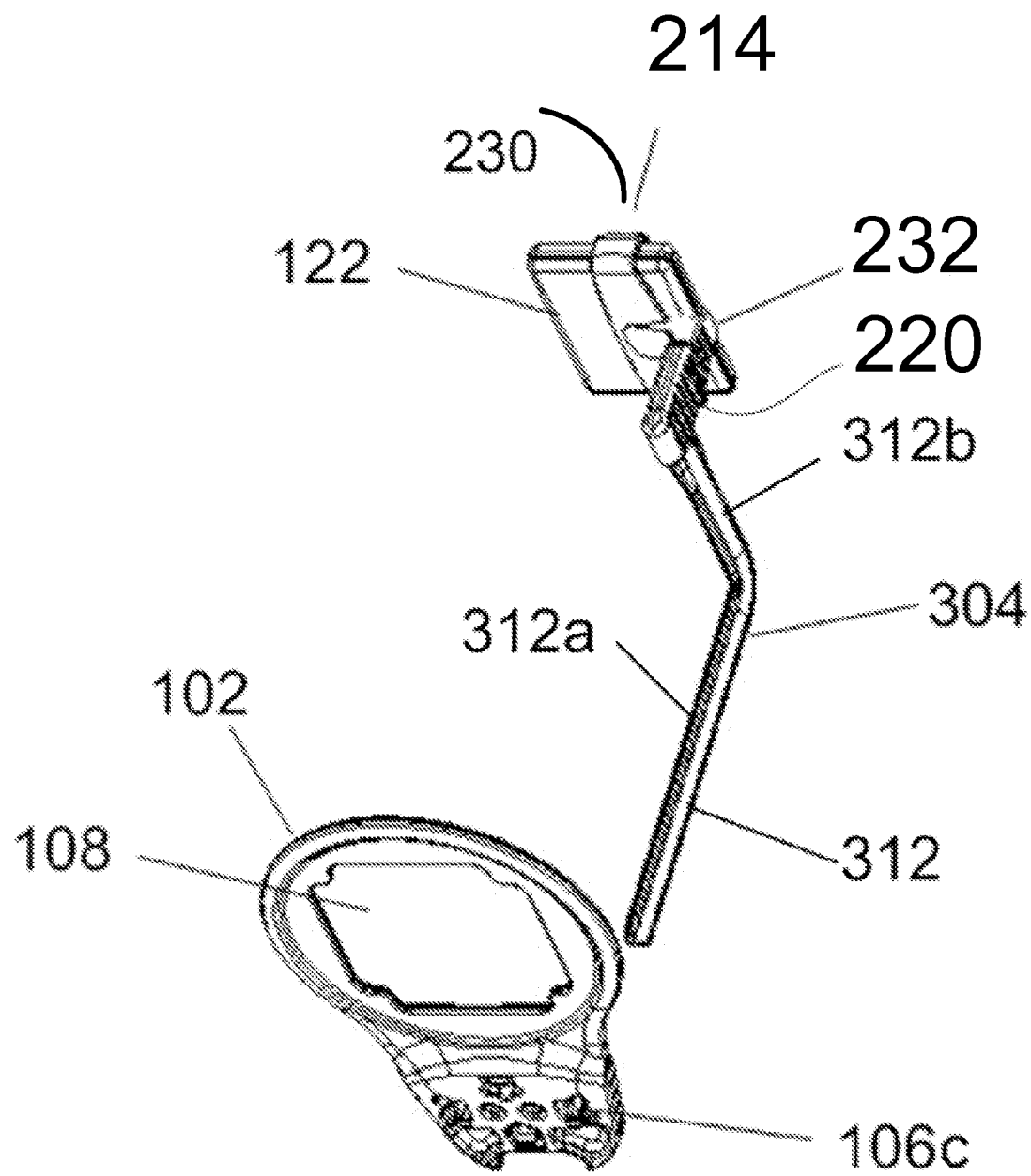
FIG. 4A illustrates an isometric assembly view of a further embodiment of a dental positioning system, as viewed from a perspective looking towards a side, rear, and top thereof, in accordance with an example aspect herein.
Figure 4B:
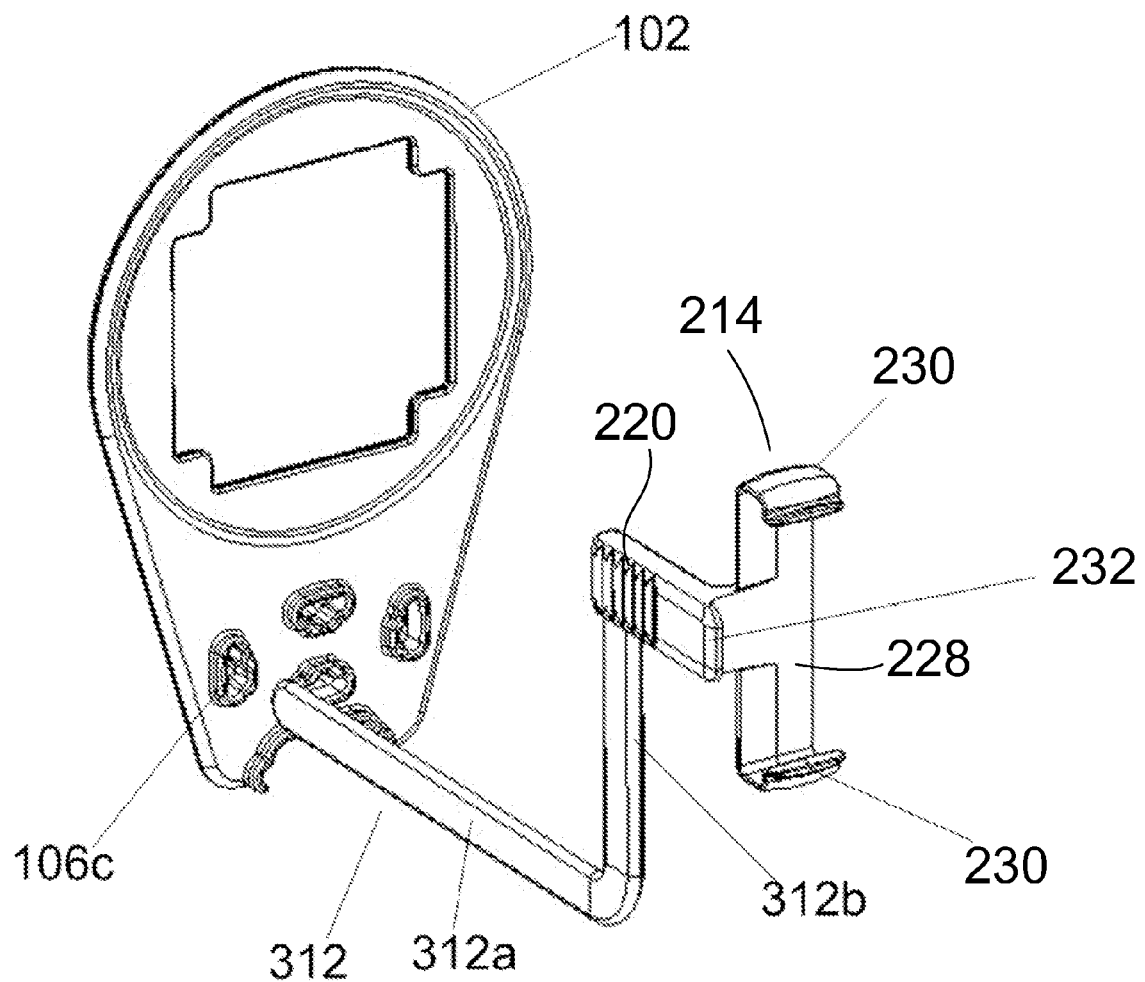
FIG. 4B illustrates the dental positioning system of FIG. 4A, as viewed from another perspective.
Figure 4C:
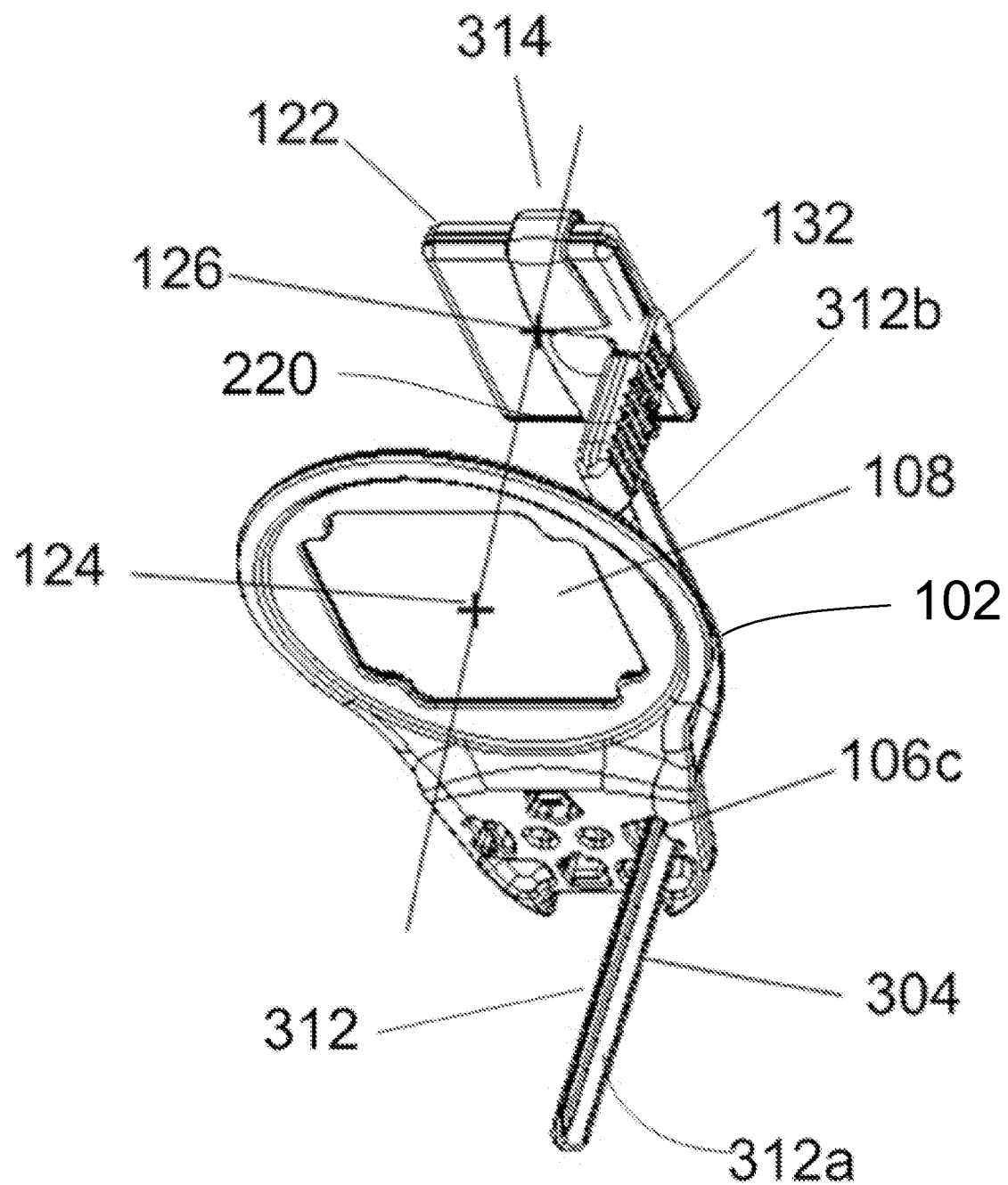
FIG. 4C illustrates the dental positioning system shown in FIG. 4A in an assembled condition, and in which the system is arranged for left-posterior x-ray images.
Figure 4D:
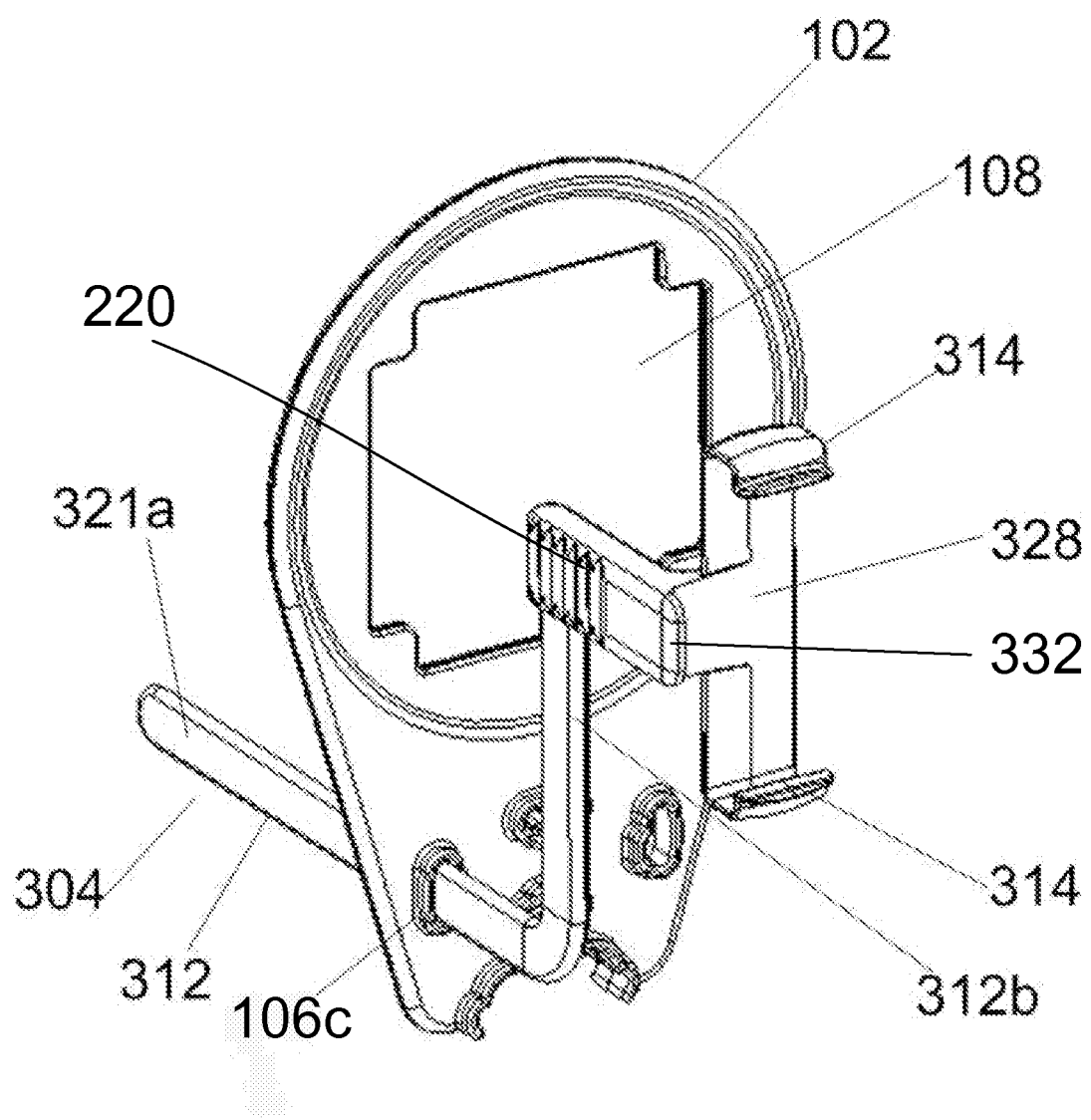
FIG. 4D illustrates the dental positioning system shown in FIG. 4C, as viewed from a perspective looking towards a side, front, and top thereof.

FIGS. 4A and 4B show the arm 312 of holder 304 aligned with opening 106c and spaced from the alignment ring 102. As shown in FIGS. 4C and 4D, opening 106c in the alignment ring 102 receives the receptor holder 304. The arm 312 of the holder 304 is formed and suitably dimensioned so that when the arm 312 is received in opening 106c and the receptor 122 is fully seated in grip 314, the receptor 122 is centered with window 108 in alignment ring 102. For example, as shown in FIG. 4C, the receptor 122 is seated in grip 314 of the holder 304 and the receptor 122 is centered with the window 108 of the alignment ring 102.

The arm 312 has a first portion 312a and a second portion 312b, which in one embodiment extend at a right angle with respect to one other. In one embodiment, the first portion 312a has a cross section that matches the shape of the opening 106c in alignment ring 102. In this manner the receptor holder 304 may be keyed with the opening 106c, in similar manner to the arrangement described herein with respect to FIGS. 1A-1C.

Thus, in at least one embodiment of the positioning system 100, each opening, 106a, 106b, and 106c, of the plurality of openings 106 of the alignment ring 102 may have a shape that is keyed to receive a corresponding arm (e.g., 112, 212, 312) of a receptor holder (e.g. 104, 204, 304) that has the same cross-sectional profile as the respective opening. For example, as discussed herein, receptor holder 104 is constructed for an anterior x-ray view and in one embodiment opening 106a in the alignment ring 102 is constructed to receive only receptor holder 104. Thus, opening 106a and holder 104 correspond to the same x-ray view, which is the anterior view. Also, as discussed herein, receptor holder 204 is constructed for a posterior, right anatomical x-ray view, and in one embodiment opening 106b in the alignment ring 102 is constructed to receive only that receptor holder 204. Thus, opening 106b and holder 204 correspond to the same x-ray view, which is the posterior, right view. Further, as described herein, receptor holder 304 is constructed for a left-posterior x-ray view, and in one embodiment the opening 106c in the alignment ring 102 is constructed to receive only that receptor holder 304. Thus, opening 106c and holder 304 correspond to the same x-ray view, which is the left-posterior view. In each of the foregoing example embodiments, when the receptor 122 is fully seated in each grip of its respective receptor holder and the receptor holder is received in its corresponding opening, the receptor 122 will be centered with the window 108 of the alignment ring 102. Moreover, owing to the keyed nature of the plurality of openings in the alignment ring 102 and the keyed profile of the arms of each receptor holder, it may be less likely or substantially not possible for a user of the system to couple the alignment ring 102 and the holder together in a way which would not center the receptor 122 in the window 108 of the alignment ring 102.

In addition to the plurality of openings 106, in one embodiment the alignment ring 102 also may be constructed with one or more other openings 206 (FIG. 2), which may each receive one or more different receptor holders.

Figure 5A:
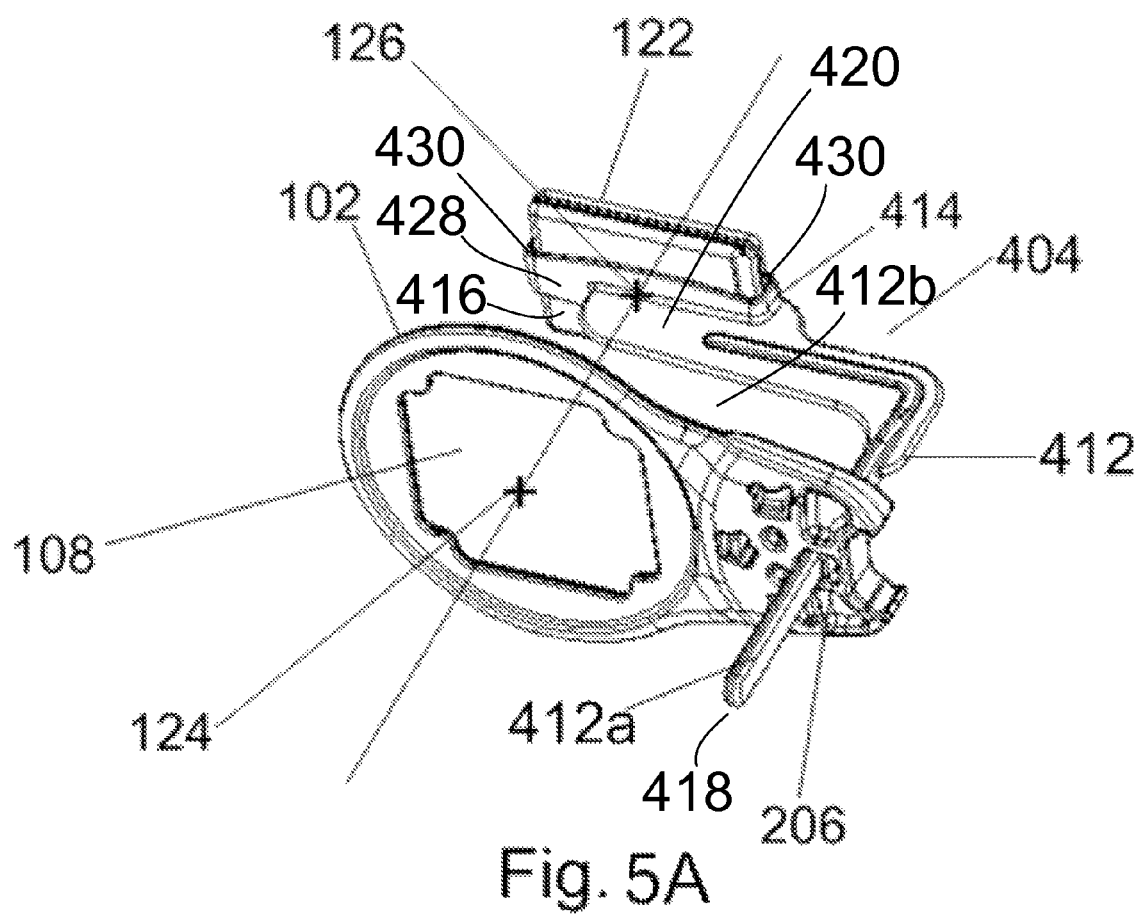
FIG. 5A illustrates an isometric view of another embodiment of a dental positioning system in accordance with an example aspect herein, as viewed from a perspective looking towards a rear and a side thereof, and which system is arranged for horizontal bitewing x-ray images.
Figure 5B:
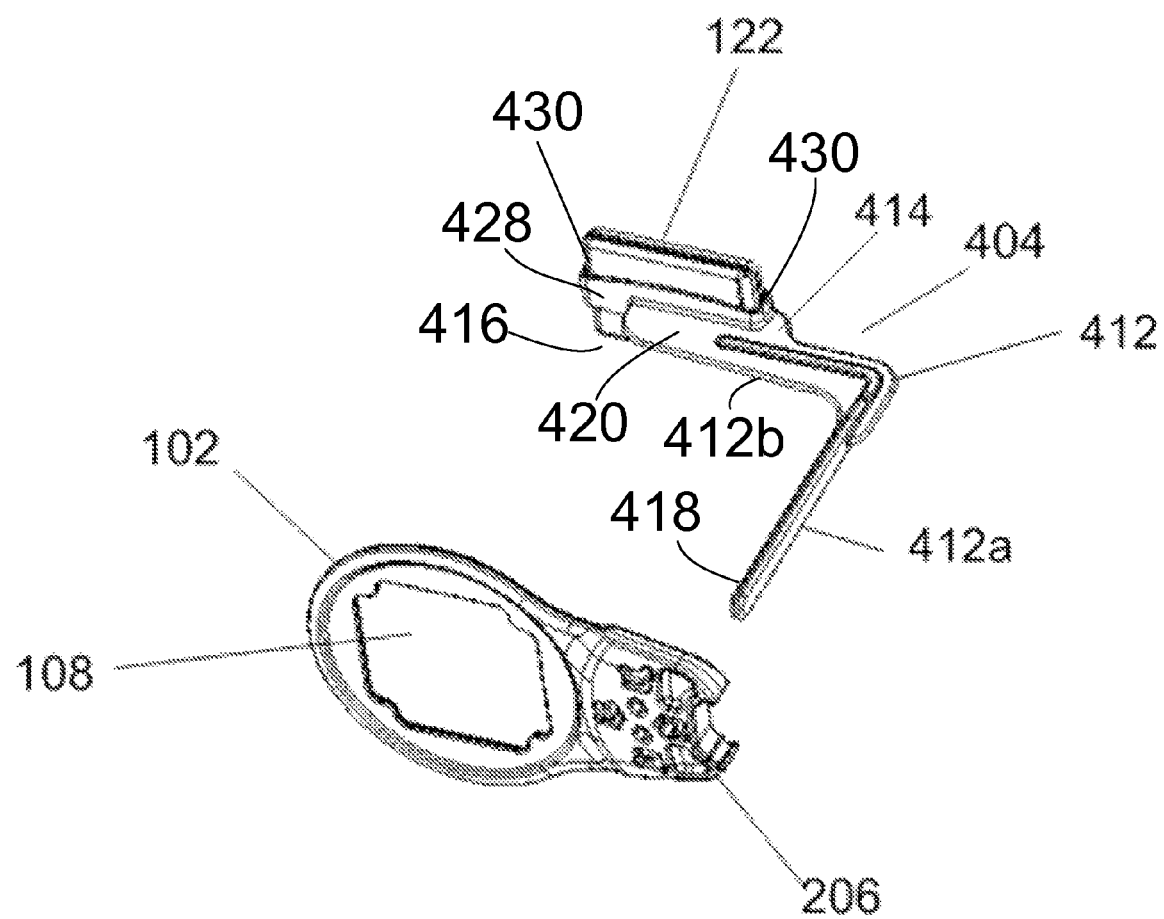
FIG. 5B. illustrates an isometric assembly view of the system of FIG. 5A.

For example, as shown in FIGS. 5A and 5B opening 206 in alignment ring 102 receives a receptor holder 404, which has an arm 412 and a grip 414 constructed to obtain horizontal bitewing x-ray images. In the embodiment shown in FIGS. 5A and 5B, the arm 412 of the receptor holder 404 has a first portion 412a extending from a free end 418 to a second portion 412b. The second portion 412b extends from the first portion 412a to the grip 414 at a second end 416. The first portion 412a and the second portion 412b extend transversely to one another. The second portion 412b includes a generally planar bite block 420 that extends from the grip 414 to the first portion 412a. The bite block 420 has two opposing planar surfaces on which a patient's teeth are received to retain the grip 414 in the patient's mouth.

The grip 414 has a base 428 and a pair of resilient fingers 430 extending from the base 428. The fingers 430 are constructed in the same manner as those of grips 114 and 214. However, unlike the receptor holders 104, 204, and 304, the grip 414 of receptor holder 404 in the embodiment shown in FIGS. 5A and 5B does not include a tab, like tabs 132 and 232, to seat against the receptor 122.

Figure 6A:
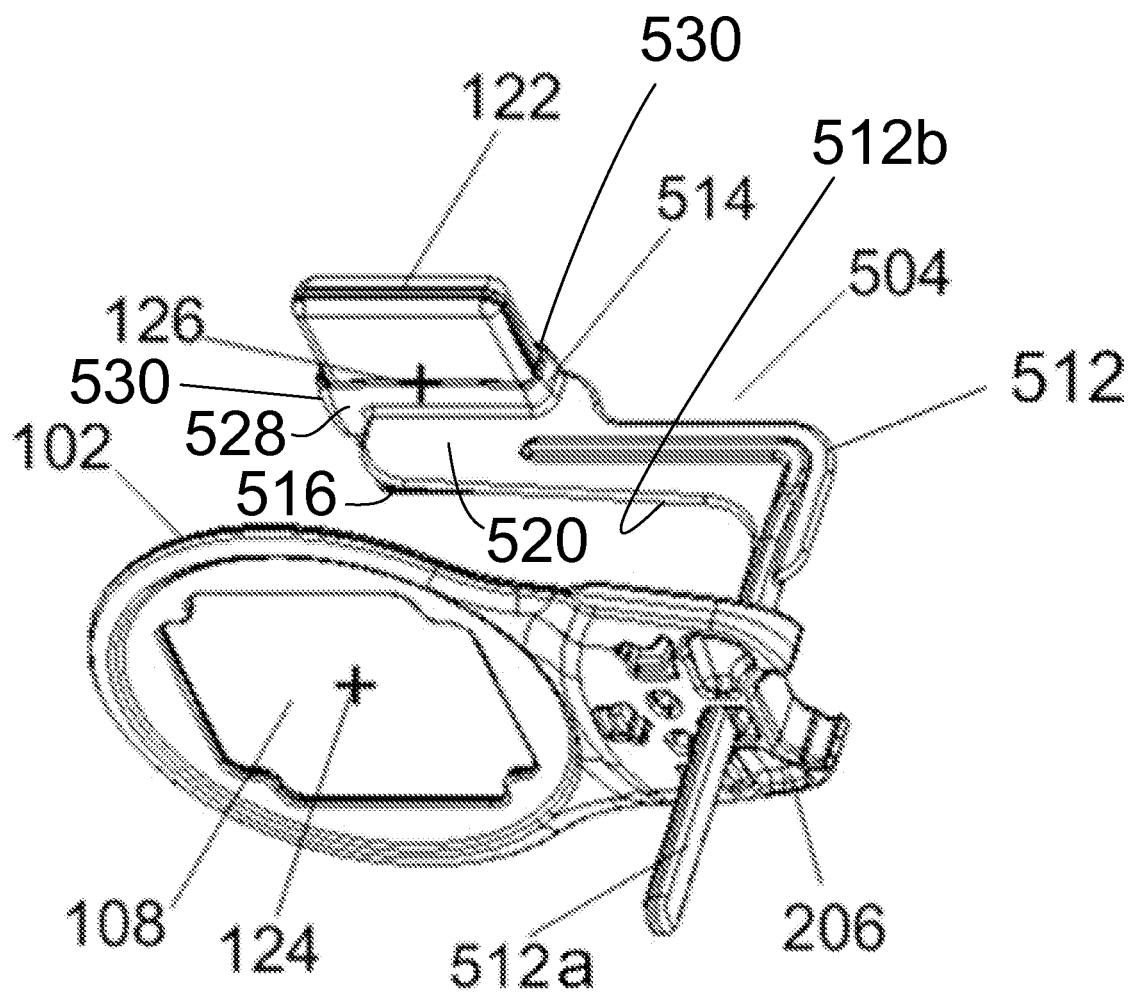
FIG. 6A illustrates an isometric view of another embodiment of a dental positioning system in accordance with an example aspect herein, and which system is assembled and arranged for vertical bitewing x-ray images.
Figure 6B:
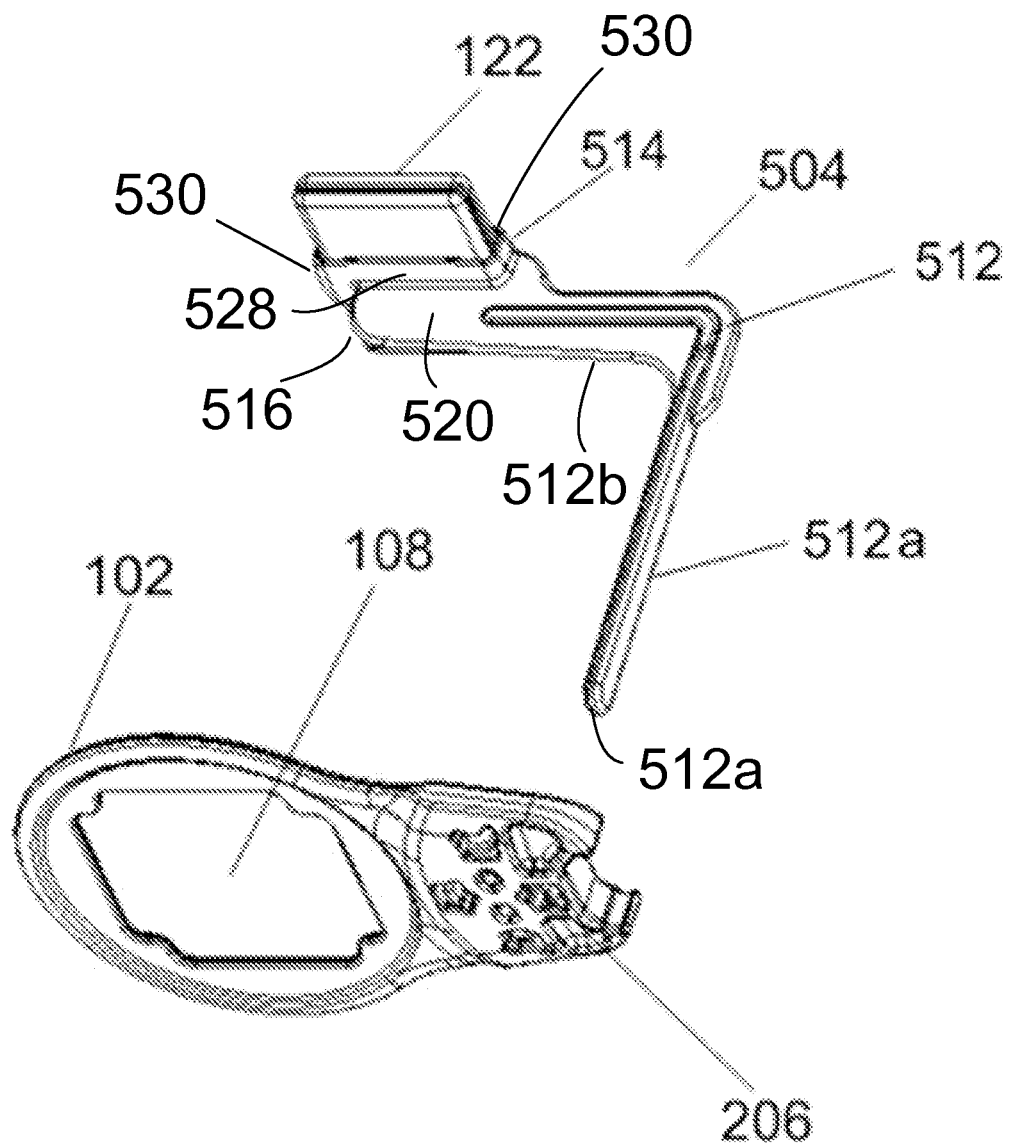
FIG. 6B illustrates the system of FIG. 6A in a disassembled state.

As shown in FIGS. 6A and 6B, opening 206 in alignment ring 102 receives another receptor holder 504, which has an arm 512 and a grip 514 constructed to obtain vertical bitewing x-ray images. In the embodiment shown in FIGS. 6A and 6B, the arm 512 of the receptor holder 504 has a first portion 512a extending from a free end 518 to a second portion 512b. The second portion 512b extends from the first portion 512a to the grip 514 at a second end 516. The first portion 512a and the second portion 512b extend transversely to one another. The second portion 512b includes a generally planar bite block 520 that extends from the grip to the first portion 512a. The bite block 520 has two opposing planar surfaces on which a patient's teeth are received to retain the grip 514 in the patient's mouth.

The grip 514 has a base 528 and a pair of resilient fingers 530 extending from the base 528. The fingers 530 are constructed in the same manner as those of grips 114 and 214. However, unlike the receptor holders 104, 204, and 304, the grip 514 of receptor holder 504 in the embodiment shown in FIGS. 6A and 6B does not include a tab, like tabs 132 and 232, to seat against the receptor 122.

The receptor holder 504 is constructed similarly to holder 404. However grip 514 is adapted to seat the receptor 122 in a different orientation to obtain vertical bitewing x-ray images. In particular, grip 514 orients the receptor 122 so that it is placed in an orientation that is offset ninety degrees as compared to the orientation shown in FIGS. 5A and 5B. Moreover, the first portions 412a and 512a of arms 412 and 512 have a common cross sectional profile that matches the shape of opening 206.

The alignment ring 102 and the receptor holders 104, 204, 304, 404, and 504 described hereinabove are, in one example, formed from a plastic, which is capable of being sterilized. The alignment ring 102 and the receptor holders can be manufactured as reusable elements or as disposable one-time-use elements, thus avoiding the need to sterilize the parts after use.

Figure 7:
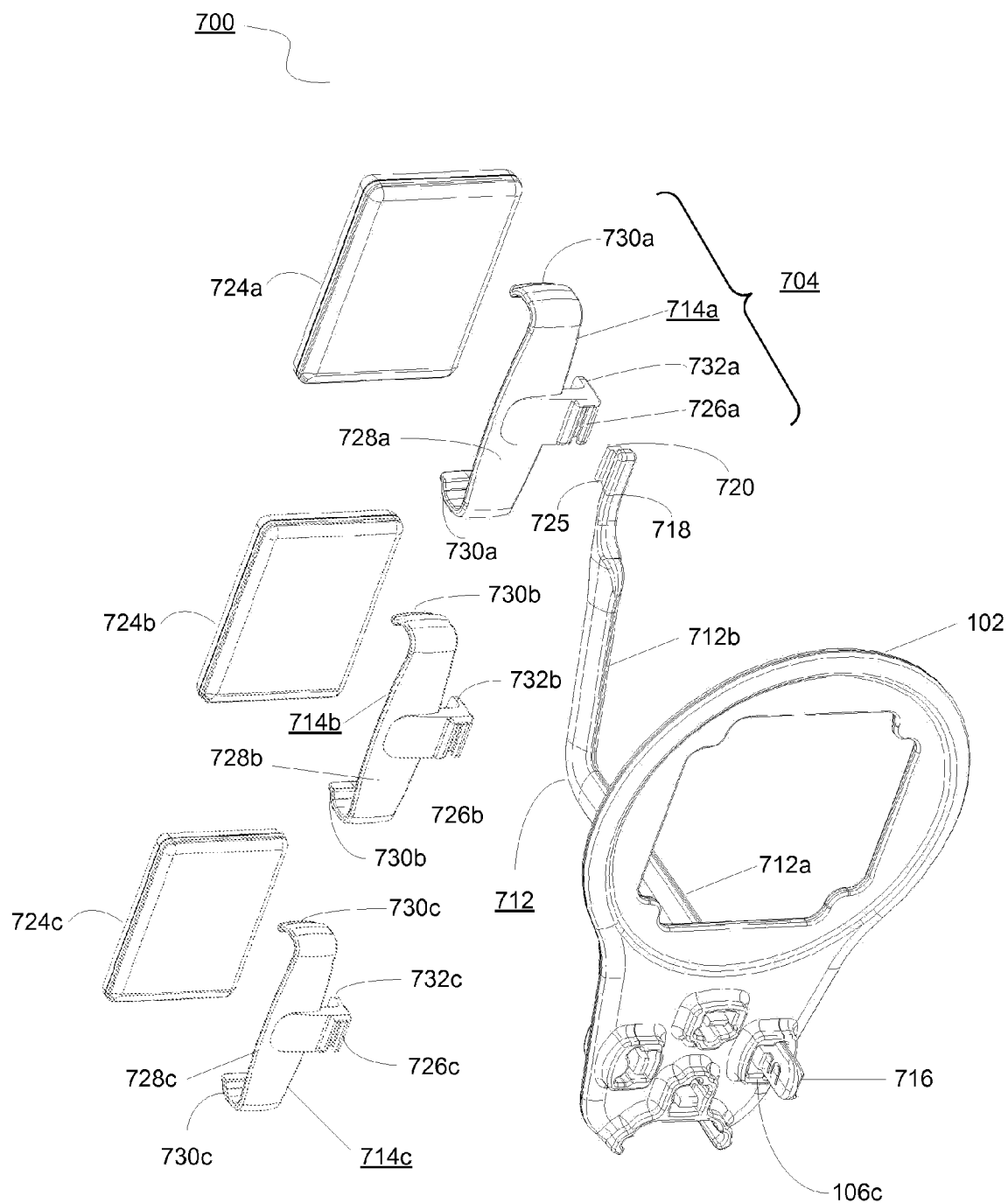
FIG. 7 illustrates an alternate arrangement of the dental positioning system shown in FIG. 4D in accordance with an example aspect herein.

FIG. 7 shows an embodiment of a dental positioning system 700 that includes a receptor holder 704, which is constructed to employ interchangeable, removable grips 714a-c, and aiming ring 102. Receptor holder 704 is constructed to obtain a left-posterior x-ray view and accordingly can be used as a substitute for receptor holder 304, described herein. While interchangeable grips 714a-c are shown arranged to form part of an alternate embodiment of receptor holder 304, it will be appreciated that alternate embodiments of the other receptor holders described herein can be similarly adapted to employ interchangeable grips in view of the following description.

Receptor holder 704 includes an arm 712 having a generally L-shape comprised of a first portion 712a extending from a free end 716 to a second portion 712b, which extends from the first portion 712a substantially in a transverse direction to its free end 718. The free end 716 of the first portion 712a is constructed to be received in opening 106c of ring 102. The first portion 712a is constructed substantially similar to the first portion 312a of receptor holder 304, and therefore, the details of the first portion 712a will not be repeated for the sake of brevity.

The free end 718 of the second portion 712b of arm 712 is constructed with an attachment 720 to receive and retain one of interchangeable grips 714a-c. The grips 714a-c are constructed similarly to grip 214 in that grips 714a-c have, respectively, a base 728a-c from which extend resilient fingers 730a-c and a tab 732a-c. Fingers 730a-c correspond to fingers 230 in construction and function while tabs 732a-c correspond to tab 232 in construction and function.

Moreover, the three grips 714a-c are each sized to receive different size receptors 724a-c, which are shown adjacent to each grip 714a-c. Each size of grips 714a-c may correspond, for example, to standard sizes of receptors, 0, 1, and 2. The free end 718 of the second portion 712b of the arm 712 has an elongated tab 725 extending along a surface of the arm 712 opposite the ring 102. The tab 725 has a generally T-shaped profile.

Each grip 714a-c has an elongated slot 726a-c that is formed on a side of base 728a-c of the grip opposite the tab 732a-c. One end of the slot 726a-c is closed. The elongated slot 726a-c has a generally T-shaped profile constructed to receive the T-shaped tab 725 of the arm 712 in sliding engagement. For example, to assemble grip 714a with arm 712, a user slides the tab 725 into the slot 726a until the tab 725 contacts the closed end of the slot 726a. The connection between tab 725 and slot 726a is constructed so that the tab 725 will be retained in the slot 726a until the receptor holder 704 is disassembled by the user by sliding the grip 714a off of the arm 712.

While particular example embodiments have been shown and described, it will be obvious to those of skill in the art that, based upon the teachings herein, changes and modifications may be made to the example embodiments without departing from these embodiments and their broader aspects. Therefore, the appended claims are intended to encompass within their scope all such changes and modifications as are within the true spirit and scope of the exemplary embodiments.

What is claimed is:

1. A dental positioning system, comprising:
a plurality of receptor holders, each receptor holder having an arm extending from a receptor grip, and each arm having a different cross-sectional profile, wherein the receptor grip includes a plurality of fingers and a tab, oriented orthogonally to the plurality of fingers, that form a slot to retain a receptor therein, and wherein the tab is constructed to contact an outer edge of the receptor when the receptor is retained in the slot; and
an alignment ring having a window formed therein and having a plurality of openings each with a different cross-sectional profile,
wherein the cross-sectional profiles of the plurality of openings respectively correspond to the cross-sectional profiles of the arms of the plurality of receptor holders, and
wherein each of the receptor holders is constructed such that when: (i) a receptor holder is received by a corresponding opening, (ii) the receptor is retained within the slot formed by the plurality of fingers and the tab, and (iii) the outer edge of the receptor is in contact with the tab, a center of the receptor is substantially centered with respect to the window.

2. The system according to claim 1, wherein the receptor includes at least one of a digital radiographic sensor and an x-ray film.

3. The system according to claim 2, wherein the digital radiographic sensor has an active area corresponding to the active area of at least one of size 0, size 1, or size 2 dental film.

4. The system according to claim 1, further comprising:
another receptor grip dimensioned to retain a different sized receptor,
wherein the receptor grip and the other receptor grip are constructed to detachably engage each of the plurality of the arms such that the receptor grip is interchangeable with another the other receptor grip.

5. The system according to claim 1, wherein each receptor holder is constructed to dispose the receptor in an oral cavity for at least one predetermined radiographic position.

6. The system according to claim 5, wherein the at least one predetermined radiographic position includes at least one of an anterior bitewing, posterior bitewing, vertical bitewing, horizontal bitewing, posterior left, and posterior right.

7. The system according to claim 1, wherein the arm of each receptor holder includes a bite block.

8. The system according to claim 1, wherein the plurality of fingers contact a second outer edge and a third outer edge of the receptor, respectively.

9. The system according to claim 8, wherein the outer edge, the second outer edge, and the third outer edge are peripheral edges of the receptor.

10. The system according to claim 1, wherein the arm of each receptor holder is constructed to extend substantially transverse from the alignment ring.

11. The system according to claim 1, wherein each opening corresponds to a radiographic receptor position associated with a corresponding receptor holder.

12. The system according to claim 1, wherein at least one of the plurality of openings in the alignment ring is beside the window.

13. The system according to claim 1, wherein the arm of each receptor holder is constructed to be slidably received in the corresponding opening.

14. The system according to claim 13, wherein each opening is constructed to receive the corresponding receptor holder from only one side of the alignment ring.

15. The system according to claim 1, wherein the alignment ring includes a notch constructed to receive a portion of a communication device.

16. The system according to claim 1, wherein the alignment ring includes a frame constructed of a material that shields x-ray radiation, and the window is formed in the frame of the alignment ring.

17. The system according to claim 1, wherein the plurality of fingers and the tab are connected to each other through a base, and wherein the base includes a slot constructed to receive a portion of an arm in sliding engagement.

18. A dental positioning method comprising:
retaining a receptor within a receptor grip, the receptor grip includes a plurality of fingers and a tab, oriented orthogonally to the plurality of fingers, that form a slot dimensioned to retain the receptor therein, wherein the receptor is retained within the slot such that an outer edge of the receptor contacts the tab, and wherein the receptor grip is disposed at one end of an arm of a receptor holder; and coupling the receptor holder to an alignment ring, having a window formed therein and having a plurality of openings each with a different cross-sectional profile, by inserting the arm of the receptor holder through an opening of the plurality of openings that has a cross-sectional profile that corresponds to a cross-sectional profile of the arm of the receptor holder, and wherein when: (i) the receptor holder is coupled to the alignment ring by insertion of the arm of the receptor holder through the opening of the plurality of openings that has the cross-sectional profile that corresponds to the cross-sectional profile of the arm of the receptor holder, (ii) the receptor is retained within the slot formed by the plurality of fingers and the tab, and (iii) the outer edge of the receptor is in contact with the tab, a center of the receptor is substantially centered with respect to the window.

\* \* \* \* \*